United States Patent
Matsuoka et al.

(10) Patent No.: US 9,897,576 B2
(45) Date of Patent: Feb. 20, 2018

(54) GAS CHROMATOGRAPHY DEVICE

(75) Inventors: Satoshi Matsuoka, Kyoto (JP);
Takahiro Nishimoto, Kyoto (JP);
Masaki Kanai, Kyoto (JP); Masanori Nishino, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 282 days.

(21) Appl. No.: 14/427,053

(22) PCT Filed: Sep. 11, 2012

(86) PCT No.: PCT/JP2012/073182
§ 371 (c)(1),
(2), (4) Date: Apr. 10, 2015

(87) PCT Pub. No.: WO2014/041597
PCT Pub. Date: Mar. 20, 2014

(65) Prior Publication Data
US 2015/0260694 A1 Sep. 17, 2015

(51) Int. Cl.
*G01N 30/30* (2006.01)
*G01N 30/54* (2006.01)
*G01N 30/16* (2006.01)

(52) U.S. Cl.
CPC ............ *G01N 30/30* (2013.01); *G01N 30/16* (2013.01); *G01N 30/54* (2013.01);
(Continued)

(58) Field of Classification Search
CPC ........ G01N 30/30; G01N 30/16; G01N 30/54; G01N 2030/3007; G01N 2030/3046
(Continued)

(56) References Cited

U.S. PATENT DOCUMENTS 5,135,549 A * 8/1992 Phillips .................. G01N 30/30
210/198.2
6,530,260 B1 3/2003 Mustacich et al.
(Continued)

FOREIGN PATENT DOCUMENTS

JP 2000-39428 A 2/2000
JP 2003-57222 A 2/2003
(Continued)

OTHER PUBLICATIONS

International Search Report dated Nov. 20, 2012, issued in corresponding application No. PCT/JP2012/073182.
(Continued)

*Primary Examiner* — Hezron E Williams
*Assistant Examiner* — Marrit Eyassu
(74) *Attorney, Agent, or Firm* — Westerman, Hattori, Daniels & Adrian, LLP

(57) ABSTRACT

A gas chromatography device includes a sample injection part, a detector, a separation column, and a transfer line connecting between the sample injection part and the separation column and between the sample injection part and the detector. Furthermore, a column temperature adjustment part for adjusting the temperature of the separation column, and a line temperature adjustment part for adjusting the temperature of the transfer line are provided. The line temperature adjustment part is structured to include a heat block which includes a heating element and which is in contact with the transfer line from one side, and a holding member which presses the transfer line toward the heat block side by being in contact from the other side, and to sandwich the transfer line by the heat block and the holding member.

18 Claims, 11 Drawing Sheets

(52) U.S. Cl.
CPC ............ *G01N 2030/3007* (2013.01); *G01N 2030/3046* (2013.01); *G01N 2030/3084* (2013.01)

(58) Field of Classification Search
USPC ...................................................... 73/23.41
See application file for complete search history.

(56) References Cited

U.S. PATENT DOCUMENTS

| | | | |
|---|---|---|---|
| 7,284,409 B2 * | 10/2007 | Hasselbrink | G01N 30/12 73/23.35 |
| 7,520,920 B1 | 4/2009 | Gregory et al. | |
| 7,654,130 B2 * | 2/2010 | Shah | G01N 30/88 73/23.35 |
| 2006/0283324 A1 * | 12/2006 | Roques | G01N 30/6095 96/101 |
| 2009/0038372 A1 | 2/2009 | Kyle et al. | |
| 2010/0256922 A1 * | 10/2010 | Roques | G01N 30/88 702/23 |
| 2012/0085148 A1 * | 4/2012 | Amirav | G01N 30/30 73/23.39 |

FOREIGN PATENT DOCUMENTS

| | | | |
|---|---|---|---|
| JP | 2004-144496 A | | 5/2004 |
| JP | 2004144496 A | * | 5/2004 |
| JP | 2008-509401 A | | 3/2008 |
| JP | 2010-536031 A | | 11/2010 |
| WO | 2006/017820 A1 | | 2/2006 |

OTHER PUBLICATIONS

Office Action dated Nov. 9, 2016, issued in counterpart Chinese Application No. 201280075621.5, with English translation. (8 pages).

* cited by examiner

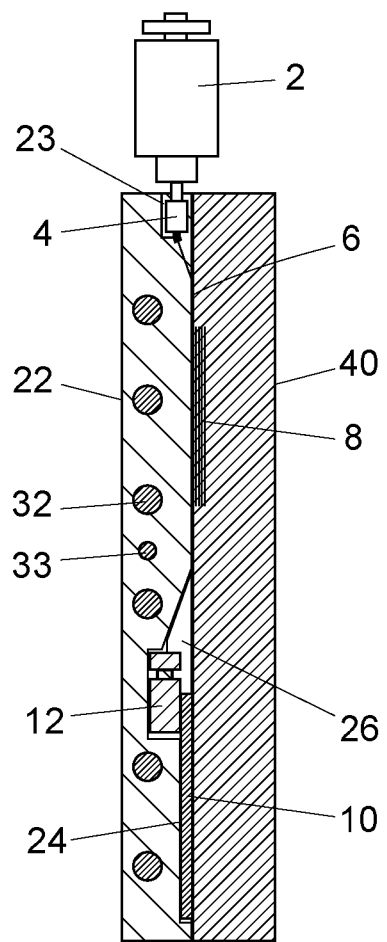

GAS CHROMATOGRAPHY DEVICE

TECHNICAL FIELD

The present invention relates to a gas chromatography device including a sample injection part, a separation column, and a detector.

BACKGROUND ART

Generally, a gas chromatograph includes a gas injection part for injecting a sample gas, a separation column for separating the sample gas into components, a detector for detecting separated sample components, and an oven. A pipe connecting between the sample injection part and the separation column and a pipe connecting between the separation column and the detector are accommodated inside the oven together with the separation column, and temperatures thereof are adjusted. The oven is a convection oven which includes a heater and a fan, and which uniformly heats the inside of the oven by circulating the air heated by the heater inside the oven.

An example of a conventional gas chromatography device will be described with reference to FIG. 8. A sample injection part 60 and a detector 64 are attached at the upper portion of an oven 74, and, in addition to a separation column 62, a capillary 66 connecting the sample injection part 60 and the separation column 62 is accommodated inside the oven 74.

The capillary 66 includes a coil form portion 68, and the coil form portion 68 constitutes a guard column or a retention gap. The guard column is inserted between the sample injection part and the separation column with the aim of preventing pollution of the separation column by impurities or high boiling point components. Regardless of presence or absence of a liquid phase is irrelevant, the length of the path of the guard column is said to have to be about 0.5 m to 5 m. Depending on the level of pollution, the guard column may have to be replaced or partially cut. The retention gap is inserted between the sample injection part and the separation column with the aim of preventing splitting of the peak of one component or spread of peak components caused due to a high injection amount of a sample in a case where an on-column method or a splitless method is used as the sample injection method. A capillary as the retention gap has to be a deactivated capillary which is not coated with a liquid phase, and the length of the path is generally said to have to be about 0.5 m to 5 m.

Generally, in the case where a guard column or a retention gap is provided between the sample injection part and the separation column, as in FIG. 8, they are accommodated inside the oven together with the separation column, and the same temperature adjustment is performed with the separation column.

As the problems regarding the gas chromatography device described above, a slow temperature increase/decrease rate of the separation column and the great power consumption due to the size of the heat capacity of the convection oven are cited. As one method of solving the problems, temperature adjustment for the separation column by another mechanism with a smaller heat capacity than the oven is proposed, by winding of a heating wire around the separation column, for example (see Patent Document 1). According to this method, since the separation column is arranged, as a column module, outside the oven by being accommodated in a separate container in a state where a heating wire is wound around the separation column, the heat capacity of a heating target is small, and the temperature of the separation column may be increased or decreased at a high rate, and thus, responsiveness to the temperature adjustment of the separation column is improved, and power consumption at the time of increasing or decreasing the temperature of the separation column is reduced.

PRIOR ART DOCUMENTS

Patent Documents

Patent Document 1: U.S. Pat. No. 6,530,260
Patent Document 2: U.S. Pat. No. 7,520,920

SUMMARY OF THE INVENTION

Problems to be Solved by the Invention

With the proposed method, however, to prevent a gasified sample from being absorbed by the inner wall of a pipe or the like, a transfer line for connecting between the sample injection part and the separation column or between the separation column and the detector has to be accommodated inside the oven, and the temperature of the transfer line has to be adjusted separately from the separation column, and thus, there is a limit on the reduction of power consumption due to the presence of the convection oven. Also, in the case of inserting the guard column or the retention gap between the sample injection part and the separation column, these are accommodated inside the convection oven. Then, if the temperatures of the guard column and the retention gap have to be increased, the actual temperature increase rates are determined by the temperature increase rate of the convection oven, and it can hardly be said that the responsiveness to temperature adjustment is improved or that the power consumption is reduced compared to a case where the separation column is accommodated inside the convection oven.

Also, in the case where a heater is wound around the capillary in the column module according to the proposed method described above, it is difficult to cut a part of the capillary, and thus, if the guard column and the retention gap are accommodated inside the column module, it is difficult to take actions such as replacement and partial cutting when the guard column or the retention gap is polluted. Accordingly, in Patent Document 1, an oven is provided separately from the column module, and the guard column and the retention gap are provided inside the oven.

To facilitate temperature adjustment of the guard column and the retention gap, it is conceivable to use a separation column chip (for example, a plate on which a path to be a column is formed by bonding glass and silicon on which a groove is etched) as the guard column and the retention gap, but even in this case, it is not possible to cut a part of an inner path of the separation column chip, and thus, it is not possible to take actions such as replacement and partial cutting when the guard column or the retention gap is polluted.

Furthermore, as another method, it is proposed to cover the periphery of a capillary constituting a transfer line by a jacket provided with a heater, and to heat the capillary by heating the air inside the jacket by the heater (see Patent Document 2). According to this method, the heating target space may be made smaller than the oven, and thus, the heat capacity of the heating target is small, and the temperature increase rate of the capillary may be increased. Also, by removing a part of the jacket, it is possible to take actions such as replacement or partial cutting of the guard column or the retention gap.

However, if the length of the capillary (the guard column or the retention gap) is long, the length, in the vertical direction, of the jacket covering the capillary becomes long, and temperature gradient in the vertical direction is caused in the space inside the jacket, and it becomes difficult to uniformly heat the entire capillary. Also, when the guard column or the like is replaced, arrangement of the coil form portion of the capillary at the same height position is not always guaranteed, and reproducibility of the temperature distribution of the capillary is not guaranteed. If there is no reproducibility of the temperature distribution of the capillary, the reproducibility of the time taken for carrier gas and a sample to pass through the capillary is also lost, and the reproducibility of the obtained chromatogram is also lost.

Moreover, if a part of the capillary is in contact with the jacket, the temperature difference will be significant between a portion of the capillary that is in contact with the jacket and a portion that is not in contact, and thus, a space of a certain size has to be reserved inside the jacket such that the capillary will not come into contact with the jacket. Accordingly, there is a limit on the reduction of the space inside the jacket, and thus, a limit on the increase in the temperature increase rate of the capillary.

Accordingly, the present invention has its aim to improve the responsiveness of the separation column and the transfer line to temperature control, and to reduce the power consumption necessary to increase or decrease the temperature of the separation column.

Solutions to the Problems

A gas chromatography device according to the present invention includes a sample injection part, a detector, a separation column, a transfer line for connecting between the sample injection part and the separation column, and between the separation column and the detector, a column temperature adjustment part including a column heating member for heating the separation column by being in contact with the separation column, and a line temperature adjustment part including a line heating member for heating the transfer line by being in contact with the transfer line and a line holding member arranged on an opposite side of the transfer line from the line heating member, the line temperature adjustment part being for adjusting temperature of the transfer line by sandwiching the transfer line by the line heating member and the line holding member.

Effects of the Invention

According to the gas chromatography device of the present invention, since the column temperature adjustment part including the column heating member, and the line temperature adjustment part for adjusting the temperature of the transfer line by sandwiching the transfer line by the line heating member and the line holding member are provided, the heat capacity of a heating target at the time of increasing the temperature of the separation column is smaller than with a convection oven, and the responsiveness of the separation column to temperature increase/decrease may be improved, and the power consumption at the time of temperature increase of the separation column may be reduced. The temperature of the transfer line may be swiftly increased by the line temperature adjustment part, and thus, temperature increase/decrease rate may be increased and the power consumption may be reduced compared to a case where the temperature of the transfer line is adjusted by an oven.

Furthermore, the present invention has a structure where the transfer line is sandwiched by the line heating member and the line holding member, and not a structure where a heater such as a heating wire is wound around the transfer line, and thus, even in a case where a guard column or a retention gap is provided, a guard column or a retention gap which is formed from a capillary that is wound in a coil form may be arranged in the line temperature adjustment part, and replacement and partial cutting of the guard column and the retention gap may be performed.

BRIEF DESCRIPTION OF THE DRAWINGS

FIG. 2 is a cross-sectional diagram of another embodiment of the gas chromatography device.

EMBODIMENTS OF THE INVENTION

Figure 1A:
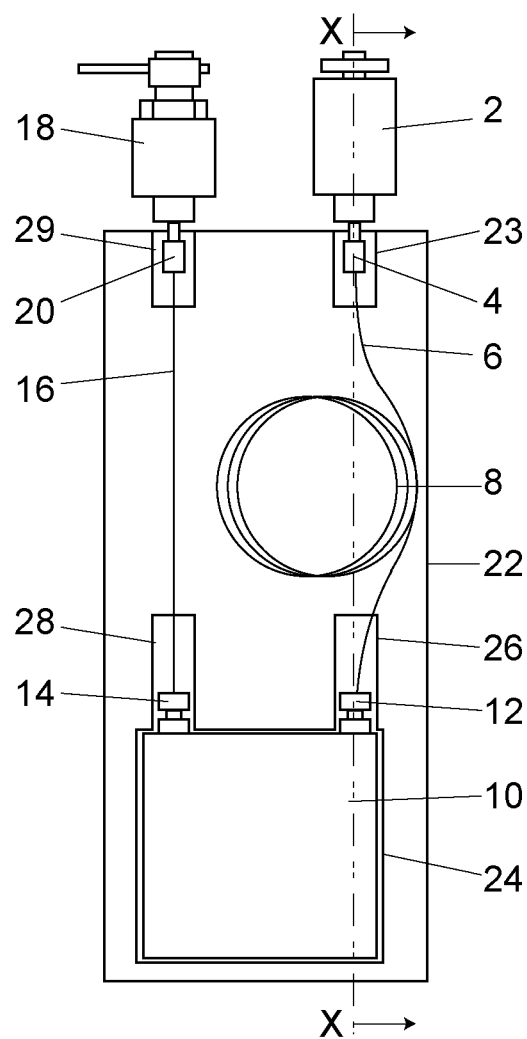
FIG. 1A is a plan view of a state where one of the holding members of an embodiment of a gas chromatography device is removed.

In a gas chromatography device of the present invention, a line holding member may be a heating member that heats a transfer line by being in contact with the transfer line. By sandwiching the transfer line by two heating members, the heating efficiency of the transfer line may be increased.

Also, the line holding member may be a flexible heat insulating member. By pressing the transfer line against a line heating member by a flexible heat insulating member, the heat from the line heating member may be efficiently transmitted to the transfer line without being lost to the surroundings, and the transfer line may be highly efficiently heated, and the responsiveness of the transfer line to temperature increase may be improved. Since one heating member having a heat source is enough, there is an advantage that the power consumption may be reduced compared to a case where the line holding member is also formed from a heating member.

In the case where the line holding member is formed from a heat insulating member, it is conceivable that a temperature difference is caused between the line heating member side and the heat insulating member side of the transfer line at the time of heating, and that a temperature distribution is caused in the transfer line. Accordingly, as a preferred embodiment, a film heat conductive member may be interposed between the transfer line and the line holding member, and a part of the heat conductive member may be brought into contact with the line heating member. This allows the heat of the line heating member to be transmitted to the heat insulating member side through the heat conductive member, and the temperature difference between the line heating member side and the heat insulating member side may be alleviated.

As an example of the heat conductive member, aluminum foil may be cited.

A column heating member and the line heating member may be formed from a common heat block. The number of parts forming the device may then be reduced, and the structure of the device may be simplified and the cost may be reduced.

In the above case, if a column temperature adjustment part is provided with a column holding member, arranged on the opposite side of a separation column from the column heating member, for sandwiching the separation column with the column heating member, the column holding member and the line holding member may also be formed from a common heat block. The number of parts forming the device may then be further reduced, and the structure of the device may be simplified and the cost may be reduced.

In the case where the column temperature adjustment part is provided with the column holding member, arranged on the opposite side of the separation column from the column heating member, for sandwiching the separation column with the column heating member, the column holding member and the line holding member may be formed from a common flexible heat insulating member. The number of parts forming the device may then be further reduced, and the structure of the device may be simplified and the cost may be reduced.

Also, the column heating member and the line heating member may be integrated while being thermally separated by having a heat insulating member sandwiched therebetween. Then, temperature adjustment of the transfer line and the separation column may be performed separately, and the degree of freedom regarding analysis may be increased; for example, analysis may be performed by increasing or decreasing the temperature of only the separation column while maintaining the temperature of the transfer line at a constant temperature.

In the above case, if the column temperature adjustment part is provided with the column holding member, arranged on the opposite side of the separation column from the column heating member, for sandwiching the separation column with the column heating member, the column holding member and the line holding member may be formed from a common flexible heat insulating member. Then, the temperature adjustment of the transfer line and the separation column may be performed separately while reducing the number of parts forming the device and simplifying the structure of the device.

Concave portions for retaining, by having fitted therein, a connection member for connecting the transfer line and the sample injection part and a connection member for connecting the transfer line and the detector are desirably provided on the surface of the line heating member that is in contact with the transfer line. The temperatures of the connection members may thereby be adjusted by a line temperature adjustment part together with the temperature of the transfer line. Moreover, by fitting the connection members in the concave portions of the line heating member so as to be retained, the connection members may be efficiently heated by the line heating member, and the connection members may be prevented from becoming cold points having lower temperatures than other portions.

In the above case, if a housing for retaining the sample injection part, the detector, and the line heating member is provided, the portions of the line heating member where the concave portions are provided are desirably attachable/detachable. Then, at the time of removing the transfer line from the line temperature adjustment part, the connection members may be exposed to the surface by simply removing the portions of the line heating member where the concave portions are provided even in a state where the sample injection part, the detector, and the line heating member are retained by the housing of the gas chromatography device, and fastening and removal of nuts forming the connection members are enabled.

Furthermore, a concave portion for retaining the separation column by having the separation column fitted therein is desirably provided on the surface of the column heating member that is in contact with the separation column. Then, the heating efficiency of the separation column by the column heating member may be increased.

Figure 1B:
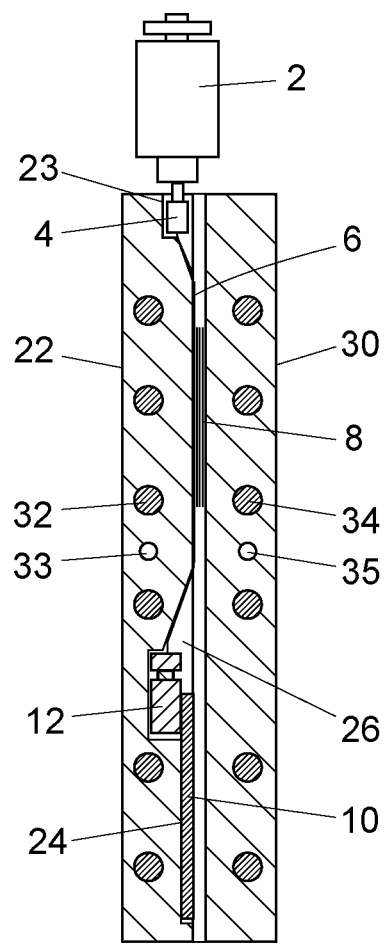
FIG. 1B is a cross-sectional diagram at the position X-X in FIG. 1A of the gas chromatography device of the embodiment.

An embodiment of the gas chromatography device will be described with reference to FIGS. 1A and 1B.

The gas chromatography device according to this embodiment includes, in addition to a sample injection part 2, a separation column chip 10, and a detector 18, a capillary 6 for connecting between the sample injection part 2 and the separation column chip 10, and a capillary 16 for connecting between the separation column chip 10 and the detector 18. In the following, the capillaries 6 and 16 form the transfer lines. The separation column chip 10 is a flat member where a solid phase and a path to be the separation column are formed to a substrate called a chip. An inlet-side connection part 12 that communicates with an end of the separation column and an outlet-side connection part 14 that communicates with the other end of the separation column are provided on one surface side of the separation column chip 10.

Additionally, in this and the following embodiments, the separation column chip formed to have a chip shape is used as the separation column, but the present invention is not limited to be such, and one that is formed by having a capillary column wound in a coil form may alternatively be used as the separation column.

An end of the capillary 6 is connected to a connection part 4 of the sample injection part 2, and the other end of the capillary 6 is connected to the inlet-side connection part 12 of the separation column chip 10. An end of the capillary 16 is connected to the outlet-side connection part 14 of the separation column chip 10, and the other end of the capillary 16 is connected to a connection part 20 of the detector 18. Each of the connection parts 4, 12, 14 and 20 is formed from a ferrule swaged to an end portion of the capillary 6 or 16 and a nut for fixing the ferrule. The ferrule and the nut form the connection member.

The capillary 6 includes a portion 8 that is wound in a coil form (hereinafter, a coil form portion). The coil form portion 8 forms the guard column or the retention gap.

The connection part 4 of the sample injection part 2, the capillaries 6 and 16, the separation column chip 10, and the connection part 20 of the detector 18 are sandwiched between a heat block 22 and a heat block 30. The heat blocks 22 and 30 are plate members of heat conductive material such as aluminum. A heater 32 and a temperature sensor 33 are embedded in the heat block 22, and a heater 34 and a temperature sensor 35 are embedded in the heat block 30. Feedback control is performed on the heater 32 based on the detected temperature of the temperature sensor 33, and on the heater 34 based on the detected temperature of the temperature sensor 35.

In this embodiment, the heat block 22 forms the column heating member and the line heating member, and the heat block 30 forms the column holding member and the line holding member. The heat blocks 22 and 30 form the line temperature adjustment part that performs temperature adjustment for the transfer line, and the column temperature adjustment part that performs temperature adjustment for the separation column chip 10.

A concave portion 23 for fitting the connection part 4, a concave portion 26 for fitting the connection part 12, a concave portion 28 for fitting the connection part 14, and a concave portion 29 for fitting the connection part 20 are provided on one surface of the heat block 22, and the connection parts 4, 12, 14 and 20 are sandwiched between the heat blocks 22 and 30 without causing a great gap between the heat blocks 22 and 30.

The heat block 22 and the heat block 30 are, for example, fixed pressed against each other by fastening of a screw that penetrates through holes provided to both of the blocks 22 and 30. Additionally, the present invention is not limited to be such, and any structure is allowed so long as two members sandwiching the transfer line are fixed pressed against each other.

FIG. 2 shows an embodiment where a heat insulating member 40 is used instead of the heat block 30 as the column holding member and the line holding member. The material of the heat insulating member 40 is desirably a flexible heat insulating material such as glass wool. By pressing the flexible heat insulating member 40 to the side of the heat block 22, the gap between the heat block 22 and the heat insulating member 40 is made small, and the air space around the connection part 4, the capillaries 6 and 16, the separation column chip 10, and the connection part 20 of the detector 18 is reduced, thus, increasing the heating efficiency. In this embodiment, there is one less heat block compared to the embodiment of FIGS. 1A and 1B, and thus, the power consumption is further reduced than in the embodiment of FIGS. 1A and 1B.

Figure 3A:
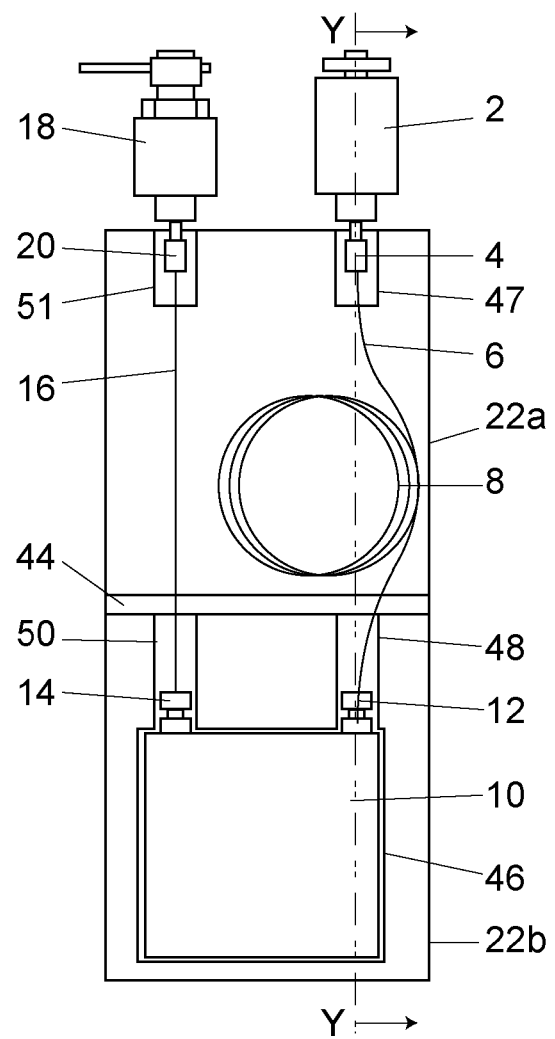
FIG. 3A is a plan view of a state where one of the holding members of, further, another embodiment of the gas chromatography device is removed.
Figure 3B:
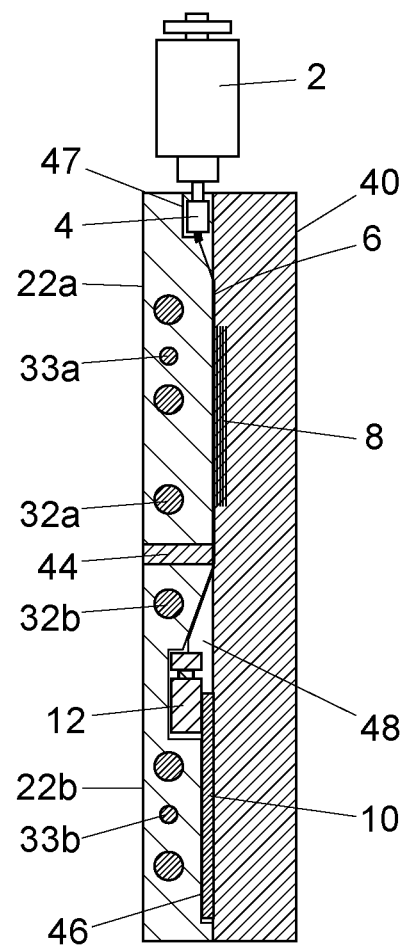
FIG. 3B is a cross-sectional diagram at the position Y-Y in FIG. 3A of the gas chromatography device of the embodiment.

Another embodiment of the gas chromatography device is shown in FIGS. 3A and 3B.

In this embodiment, a heat block 22a as the line heating member and a heat block 22b as the column heating member that are integrated with a heat insulating member 44 interposed therebetween is used instead of the heat block 22 according to the embodiment in FIG. 2. One surface of the heat block 22a is mainly in contact with the connection parts 4 and 20 and the capillaries 6 and 16, and one surface of the heat block 22b is mainly in contact with the separation column chip 10. The heat blocks 22a and 22b are thermally separated by the heat insulating member 44.

The heat block 22a is provided with a heater 32a and a temperature sensor 33a, the heat block 22b is provided with a heater 32b and a temperature sensor 33b, and the heat blocks 22a and 22b are configured in such a way that temperatures may be independently adjusted. The heat block 22a forms the line temperature adjustment part with the heat insulating member 40, and the heat block 22b forms the column temperature adjustment part with the heat insulating member 40.

By thermally separating the heat block 22a that is mainly in contact with the transfer line and the heat block 22b that is mainly in contact with the separation column chip 10 and allowing mutually independent temperature adjustment, as described above, the degree of freedom regarding analysis may be increased; for example, analysis may be performed by increasing or decreasing the temperature of the separation column chip 10 in a state where the temperature of the transfer line is maintained constant.

Concave portions 47 and 51 for fitting the connection parts 4 and 20, respectively, are provided on one surface of the heat block 22a. A concave portion 46 for fitting the separation column chip 10, and concave portions 48 and 50 for fitting the connection parts 12 and 14, respectively, are provided on one surface of the heat block 22b.

Figure 4:
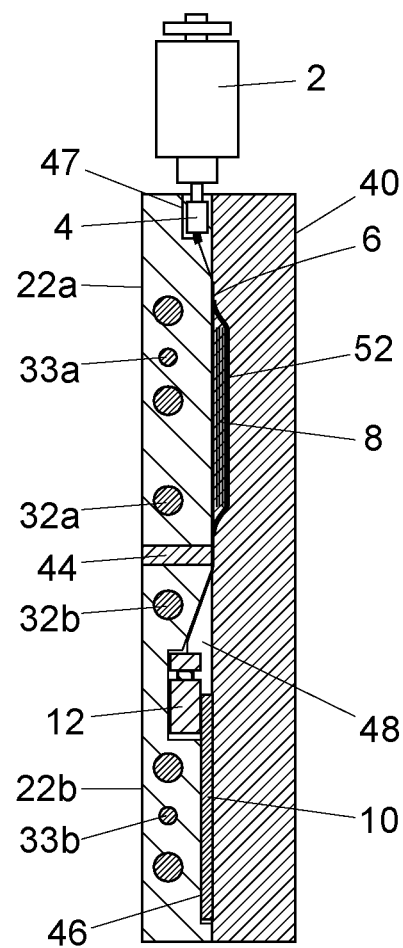
FIG. 4 is a cross-sectional diagram of, further, another embodiment of the gas chromatography device.

Further another embodiment is shown in FIG. 4.

According to the embodiment of FIG. 4, a film heat conductive member 52 of aluminum foil is interposed between the coil form portion 8 and the heat insulating member 40 to increase the heating efficiency of the coil form portion 8 of the capillary 6 according to the embodiment of FIG. 3. The heat conductive member 52 is provided having a size big enough to cover the entire coil form portion 8 from the side of the heat insulating member 40, and its end portion is in contact with the heat block 22a. The heat of the heat block 22a is thereby transferred to the side of the heat insulating member 40 of the coil form portion 8, and the entire coil form portion 8 is uniformly heated. Additionally, as the film heat conductive member 52, any flexible material with a low heat capacity and high heat conductivity may be used; for example, steel wool formed into a film shape may be used instead of the aluminum foil.

Figure 5:
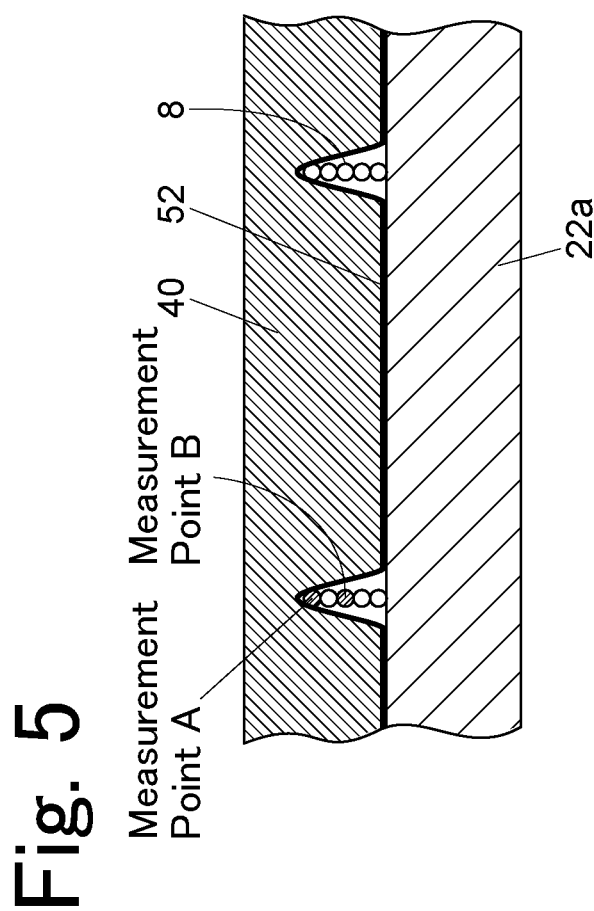
FIG. 5 is a diagram for describing a temperature measurement position at a time of measurement of temperature of a guard column portion using the gas chromatography device of the embodiment.

As shown in FIG. 5, to measure the effect that is obtained by interposing the heat conductive member 52 between the coil form portion 8 and the heat insulating member 40, temperature is measured using, as the capillary forming the coil form portion 8, a capillary having a large diameter called a wide bore capillary having an inner diameter of 0.53 mm, and inserting a thermocouple in such a way as to come into contact with both the capillary at the position of the coil form portion 8 closest to the heat insulating member 40 (a measurement point A) and the capillary positioned in the middle of the heat block 22a and the heat insulating member 40 (a measurement point B). A platinum sensor is used as the temperature sensor 33a of the heat block 22a, and the heater 32a is controlled in such a way that the measurement value is increased from 50° C. to 350° C. at the rate of 20° C./min, and then, is made steady at 350° C. Data of the temperature differences between each of the measurement points A and B and the heat block 22a is shown in FIG. 6.

Figure 6:
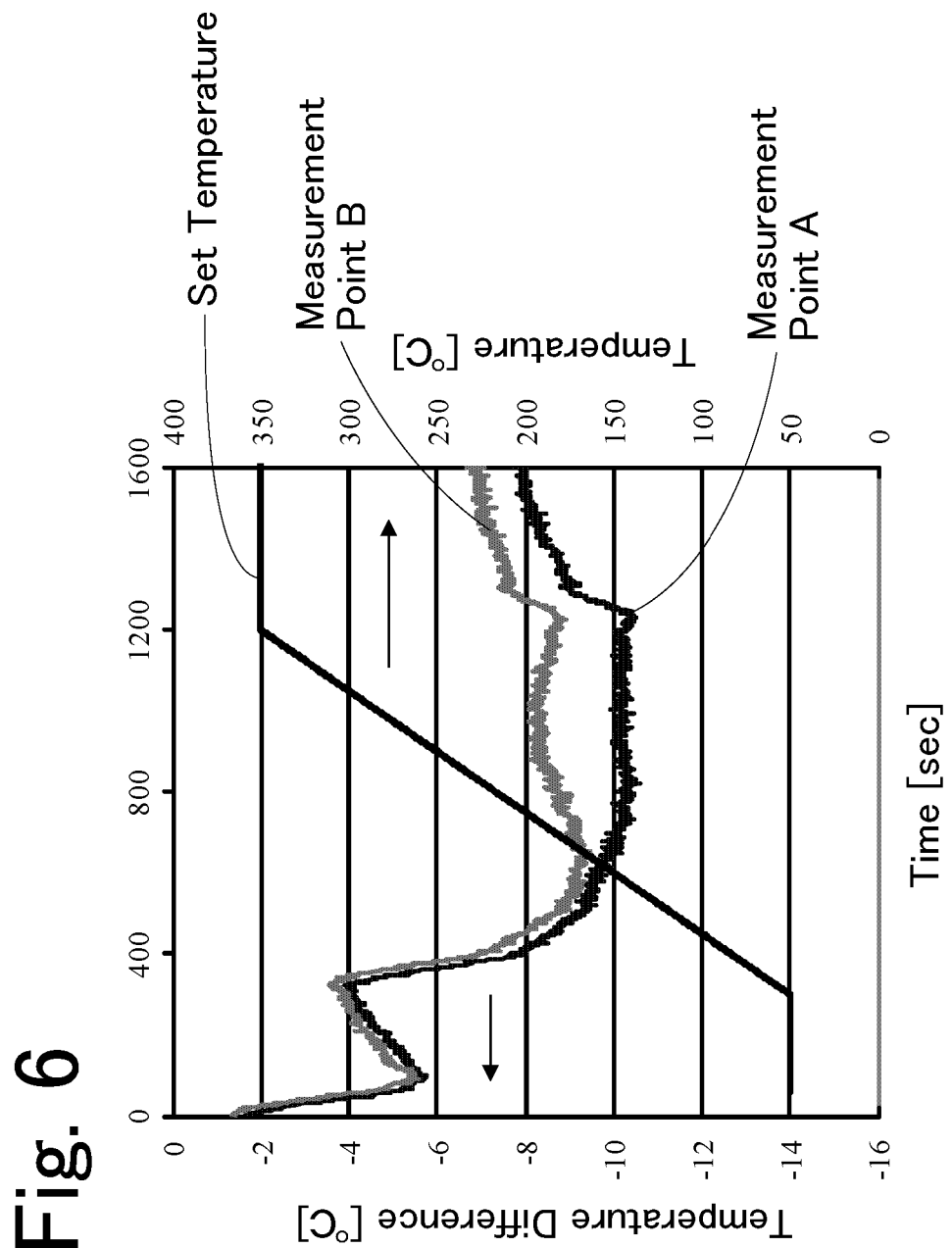
FIG. 6 is measurement data at a time of measurement of temperature of the guard column portion using the gas chromatography device of the embodiment.

As shown in FIG. 6, the temperature at the measurement point A is, at the maximum, about 10° C. lower than the temperature of the heat block 22a at the time of temperature increase, and at the maximum, about 8° C. lower in the steady state at 350° C. The temperature at the measurement point B is, at the maximum, about 9° C. lower than the temperature of the heat block 22a at the time of temperature increase, and at the maximum, about 7° C. lower in the steady state at 350° C. From these results, it can be said that the temperature difference between each of the measurement points A and B and the heat block 22a is about 10° C. at the maximum, and that the capillary forming the coil form portion 8 is sufficiently heated uniformly under this measurement condition. Additionally, if the temperature at the measurement point A or B has to be made closer to a set temperature, it is enough if the set temperature of the heat block 22a at the time of temperature increase is set to be higher by about 10° C. In the embodiment of FIG. 4, the heat blocks 22a and 22b are thermally separated by a heat insulating material 44, and thus, temperature control of the separation column chip 10 is not affected even if the set temperature of the heat block 22a is set higher.

Additionally, the case of providing the film heat conductive member 52 is not restricted to a case where a guard column or a retention gap such as the coil form portion 8 is provided, and such a heat conductive member may be used to increase the heating efficiency of the entire transfer line in a case where the guard column or the retention gap is not provided.

Furthermore, the embodiment of FIG. 4 is the embodiment of FIGS. 3A and 3B to which the heat conductive member 52 is added, but the present invention may be applied, without being limited to the case described above, to a case where the line holding member is configured by the heat insulating member. By adding a flexible film heat conductive member between the transfer line and the line holding member formed of the heat insulating member, the temperature distribution caused in the space between the line heating member and the heat insulating member may be alleviated.

Although not shown, the sample injection part 2, the detector 18, and the heat blocks (the line heating member and the column heating member) 22, 22a and 22b of the embodiments described above are fixed to the housing of the gas chromatography device. The capillaries 6 and 16 may have to be replaced due to reasons such as pollution. Replacement of the capillaries 6 and 16 has to be performed by removing the heat block 30 or the heat insulating member 40 as the column holding member, but operations such as removal and fastening of nuts forming the connection members 4 and 20 are difficult when only the heat block 30 or the heat insulating member 40 is removed.

Figure 7A:
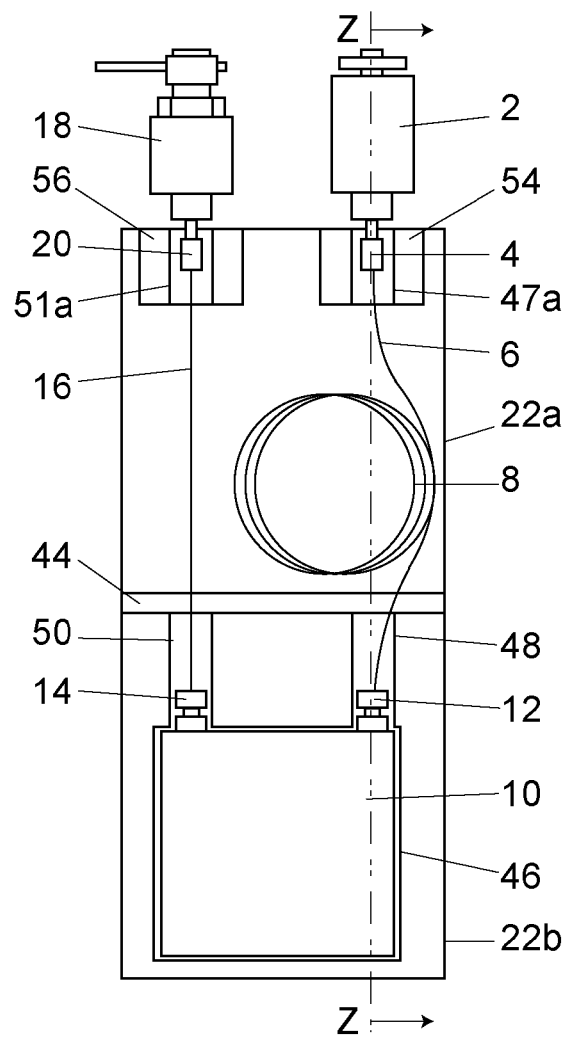
FIG. 7A is a plan view of a state where one of the holding members of, further, another embodiment of the gas chromatography device is removed.
Figure 7B:
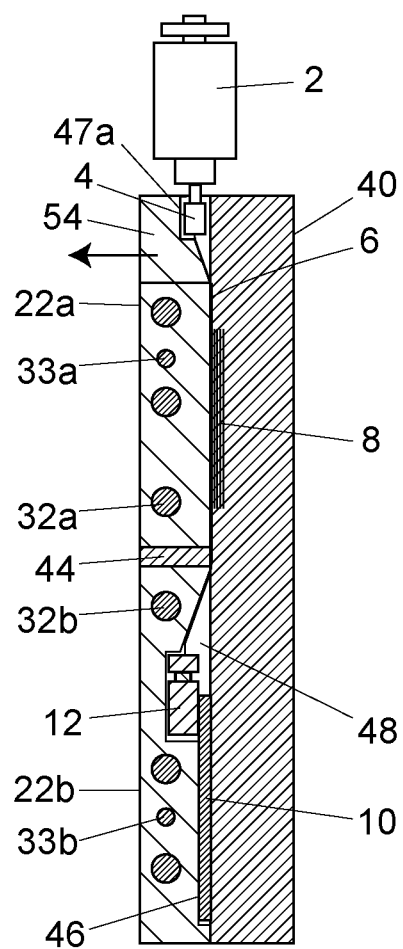
FIG. 7B is a cross-sectional diagram at the position Z-Z in FIG. 7A of the gas chromatography device of the embodiment.
Figure 8:
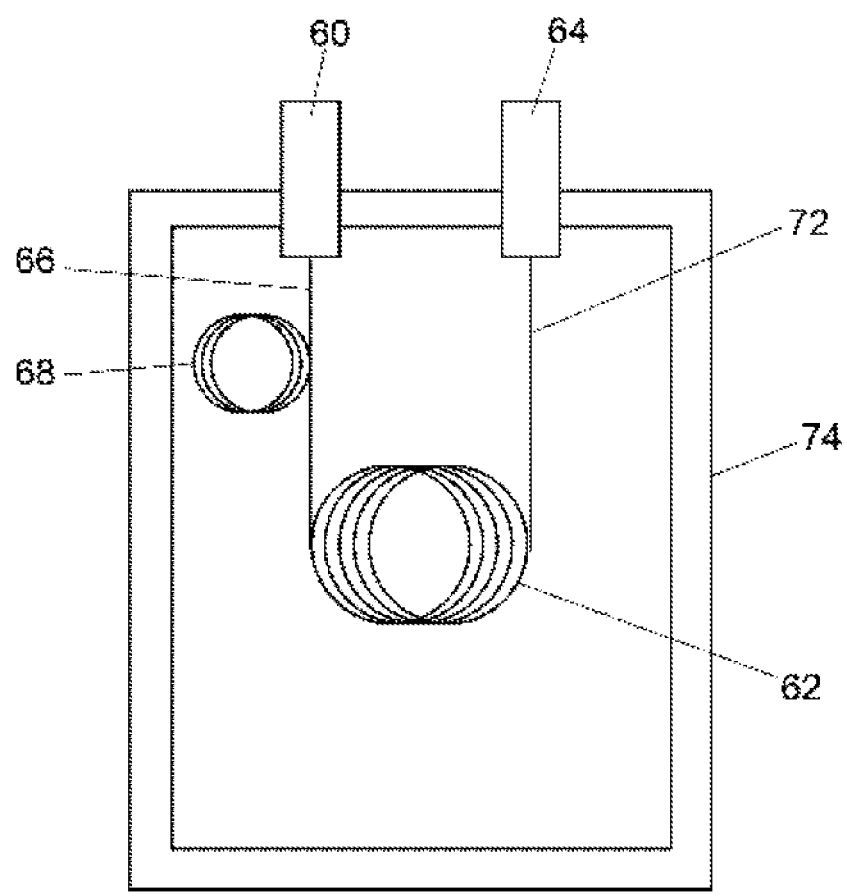
FIG. 8 is a schematic configuration diagram showing an example of a conventional gas chromatography device.

FIGS. 7A and 7B show an embodiment where a structure for facilitating replacement of the capillaries 6 and 16 of the embodiment of FIGS. 3A and 3B is provided. Portions 54 and 56 of the heat block 22a for retaining the connection members 4 and 20 may be removed in the direction of the arrow shown in FIG. 7B, and operations of removing or fastening the nuts forming the connection members 4 and 20 is facilitated by removing these portions 54 and 56 and the heat insulating member 40. This structure is not limited to the structure of FIG. 7A or 7B, and may be applied to any of the embodiments described above.

The portions 54 and 56 form parts of the heat block 22a, and when integrated with the heat block 22a, may transfer the heat from the heater 32a to the connection members 4 and 20 by being sufficiently in contact with other parts of the heat block 22a.

Additionally, the portions 54 and 56 may be thermally independent from the heat block 22a, and may be provided with their own heater and temperature sensor.

DESCRIPTION OF REFERENCE SIGNS

2: Sample injection part
4, 20: Connection member
6, 16: Capillary (transfer line)
8: Coil form portion (guard column or retention gap)
10: Separation column chip
12: Inlet-side connection part (separation column)
14: Outlet-side connection part (separation column)
18: Detector
22, 22a, 22b, 30: Heat block
23, 24, 26, 28, 29, 47, 47a, 48, 50, 51, 51a: Concave portion
32, 32a, 32b, 34: Heater
33, 33a, 33b, 35: Temperature sensor
40, 44: Heat insulating member
52: Heat conductive member

What is claimed is:

1. A gas chromatography device comprising:
a sample injection part;
a detector;
a separation column;
a first transfer line for connecting between the sample injection part and the separation column, and a second transfer line for connecting between the separation column and the detector;
a column temperature adjustment part including a column heating member for heating the separation column by being in contact with the separation column; and
a line temperature adjustment part including a line heating member for heating the first and second transfer lines by being in contact with the first and second transfer lines and a line holding member arranged on an opposite side of the first and second transfer lines from the line heating member, the line temperature adjustment part being for adjusting temperature of the first and second transfer lines by sandwiching the first and second transfer lines by the line heating member and the line holding member,
wherein a film heat conductive member is interposed between the first and second transfer line and the line holding member, and a part of the film heat conductive member is in contact with the line heating member.

2. The gas chromatography device according to claim 1, wherein the line holding member is a heating member for heating the transfer line by being in contact with the transfer line.

3. The gas chromatography device according to claim 2, wherein the column heating member and the line heating member are formed from a common heat block.

4. The gas chromatography device according to claim 3, wherein the column temperature adjustment part includes a column holding member, arranged on an opposite side of the separation column from the column heating member, for sandwiching the separation column with the column heating member, and
wherein the column holding member and the line holding member are formed from a common heat block.

5. The gas chromatography device according to claim 3, wherein the column temperature adjustment part includes a column holding member, arranged on an opposite side of the separation column from the column heating member, for sandwiching the separation column with the column heating member, and
wherein the column holding member and the line holding member are formed from a common flexible heat insulating member.

6. The gas chromatography device according to claim 2, wherein the column heating member and the line heating member are integrated while being thermally separated by having a heat insulating member sandwiched therebetween.

7. The gas chromatography device according to claim 6, wherein the column temperature adjustment part includes a column holding member, arranged on an opposite side of the separation column from the column heating member, for sandwiching the separation column with the column heating member, and wherein the column holding member and the line holding member are formed from a common flexible heat insulating member.

8. The gas chromatography device according to claim 1, wherein the line holding member is a flexible heat insulating member.

9. The gas chromatography device according to claim 8, wherein the column heating member and the line heating member are formed from a common heat block.

10. The gas chromatography device according to claim 9, wherein the column temperature adjustment part includes
a column holding member, arranged on an opposite side of the separation column from the column heating member, for sandwiching the separation column with the column heating member, and
wherein the column holding member and the line holding member are formed from a common heat block.

11. The gas chromatography device according to claim 9, wherein the column temperature adjustment part includes
a column holding member, arranged on an opposite side of the separation column from the column heating member, for sandwiching the separation column with the column heating member, and
wherein the column holding member and the line holding member are formed from a common flexible heat insulating member.

12. The gas chromatography device according to claim 8, wherein the column heating member and the line heating member are integrated while being thermally separated by having a heat insulating member sandwiched therebetween.

13. The gas chromatography device according to claim 12,
wherein the column temperature adjustment part includes
a column holding member, arranged on an opposite side of the separation column from the column heating member, for sandwiching the separation column with the column heating member, and
wherein the column holding member and the line holding member are formed from a common flexible heat insulating member.

14. The gas chromatography device according to claim 1, wherein the heat conductive member is aluminum foil.

15. The gas according to claim 1, wherein concave portions for retaining, by having fitted therein, a connection member for connecting the transfer line and the sample injection part and a connection member for connecting the transfer line and the detector are provided on a surface of the line heating member that is in contact with the transfer line.

16. The chromatography device according to claim 15, comprising:
a housing for retaining the sample injection part, the detector, and the line heating member, wherein portions of the line heating member where the concave portions are provided are attachable/detachable.

17. The chromatography device according claim 1, wherein a concave portion for retaining, by having fitted therein, the separation column is provided on a surface of the column heating member that is in contact with the separation column.

18. The gas chromatography device according to claim 1,
wherein the line temperature adjustment part is further configured to adjust temperature of a connection member for connecting the transfer line and the sample injection part and a connection member for connecting the transfer line and the detector.

* * * * *